United States Patent
During

(10) Patent No.: US 9,351,968 B1
(45) Date of Patent: May 31, 2016

(54) METHODS OF TREATING DEVELOPMENTAL DISORDERS USING PIPRADROL

(71) Applicant: Ovid Therapeutics Inc., New York, NY (US)

(72) Inventor: Matthew During, Weston, CT (US)

(73) Assignee: OVID THERAPEUTICS INC, New York, NY (US)

( * ) Notice: Subject to any disclaimer, the term of this patent is extended or adjusted under 35 U.S.C. 154(b) by 0 days.

(21) Appl. No.: 14/876,110

(22) Filed: Oct. 6, 2015

Related U.S. Application Data

(60) Provisional application No. 62/215,831, filed on Sep. 9, 2015.

(51) Int. Cl.
*A61K 31/4458* (2006.01)
*A61K 45/06* (2006.01)

(52) U.S. Cl.
CPC .............. *A61K 31/4458* (2013.01); *A61K 45/06* (2013.01)

(58) Field of Classification Search
CPC .................................................. A61K 31/4458
USPC ........................................................ 514/217
See application file for complete search history.

(56) References Cited

PUBLICATIONS

Chen et al., J. Pharmacology Experimental Therapeutics (1958), vol. 123, pp. 212-215.*
GuideChem, CAS Database, pp. 1-2, Aug. 28, 2009.*
Howard D. Fabing, "Clinical Experience with Meratran (A New Central Nervous System Stimmulant)", Diseases of the Nervous System, vol. XVI, No. 1, Jan. 1955; pp. 10-15.
Rickels et al., "Pipradrol in Mild Depression: A Controlled Study", The Journal of Clinical Pharmacology, Feb.-Mar. 1974, pp. 127-133.
White, et al, "Pipradrol and Pipradrol Derivatives", Novel Psychoactive Substances, Elsevier, 2013, Chapter 10; pp. 233-259.
Kistner et al., "Use of Pipradrol in Obstetrics and Gynecology", The New England Journal of Medicine, vol. 254, No. 11, Mar. 15, 1956; pp. 507-510.
Leon Oettinger, Jr., M.D., "Meratran—Preliminary Report of a New Drug for the Treatment of Behavior Disorders in Children", Diseases of the Nervous System, Oct. 1955; pp. 299-302.

* cited by examiner

*Primary Examiner* — Taofiq A Solola
(74) *Attorney, Agent, or Firm* — Carter, DeLuca, Farrell & Schmidt, LLP

(57) ABSTRACT

Methods of treating developmental disorders by administering a pharmaceutical composition of pipradrol or a pharmaceutically acceptable salt thereof are provided. The methods may be used to treat conditions such as epilepsy, Landau-Kleffner Syndrome, Lennox-Gastaut syndrome (LGS) and Dravet syndrome.

4 Claims, No Drawings

METHODS OF TREATING DEVELOPMENTAL DISORDERS USING PIPRADROL

CROSS-REFERENCE TO RELATED APPLICATION

The present application claims the benefit of and priority to U.S. Provisional Application Ser. No. 62/215,831, filed on Sep. 9, 2015, the entire contents of which are herein incorporated by reference.

TECHNICAL FIELD

Methods of using a composition including pipradrol, a derivative thereof, or a pharmaceutically acceptable salt thereof for the treatment of developmental disorders in a subject in need thereof.

BACKGROUND

Pipradrol is a mild central nervous system stimulant that acts on both dopamine and norepinephrine reuptake. It was originally marketed as Meratran® (Wm. S. Merrell Co of Cincinnati Ohio) and also in combination with several vitamins as Alertonic® Elixir. Pipradrol was considered an "energetic" when it first came to market in the mid to late 1950's and used for obesity, narcolepsy, and depression. Pipradrol has also been used in the setting of obstetric and gynecological practice, with multiple benefits, for example improving nausea and vomiting, premenstrual symptoms, post-partum psychosis, and menopausal-associated depression Kistner and Duncan, *The New England Journal of Medicine* 254, 507-510 (1956).

There is limited evidence that suggests pipradrol may have some efficacy in behavioral disorders in children. Oettinger, *Diseases of the Nervous System* 16, 299-302 (1955). The report concludes that the action of pipradrol lies in increasing the attention span and decreasing irritability with a resultant increase in function. However, pipradrol has been associated with side effects such as anxiety and alertness at bedtime. Fabing, *Diseases of the Nervous System* 10-15 (January 1955). In addition, although some anticonvulsant activity has been suggested, high doses of pipradrol may cause incoordinated activity and ataxia, followed by tremors and clonic convulsions. Following the Kefauver-Harris amendments to the FDA act in 1962, pipradrol was one of thousands of drugs that were assessed by special committees to define whether there was sufficient safety and efficacy to remain an approved drug. This process was called the Drug Efficacy Study Initiative or DESI. The committee which reviewed pipradrol included the psychiatrist Karl Rickels, who had published a study on 111 individuals with depression, in which pipradrol was not superior to placebo (Rickels et al., *The Journal of Clinical Pharmacology* 14, 127-133; 1974). As a result, pipradrol was removed from the FDA register of approved drugs.

There remains a need for improved methods of treating developmental disorders including Scn1a-related disorders.

SUMMARY

Methods of treating a developmental disorder by administering to a patient in need thereof a pharmaceutical composition of pipradrol or a pharmaceutically acceptable salt thereof.

In embodiments, methods are provided for treatment of developmental disorders including epilepsy, Landau-Kleffner Syndrome, Lennox-Gastaut syndrome (LGS) and Dravet syndrome by administering to a patient in need thereof a pharmaceutical composition of pipradrol or a pharmaceutically acceptable salt thereof.

In embodiments, methods are provided for treatment of developmental disorders including benign rolandic epilepsy (BRE), intractable childhood epilepsy (ICE), childhood absence epilepsy (CAE), juvenile myoclonic epilepsy (JME), infantile spasms (or West syndrome) and Lennox-Gastaut syndrome (LGS) by administering to a patient in need thereof a pharmaceutical composition of pipradrol or a pharmaceutically acceptable salt thereof.

In embodiments, methods are provided for treatment of developmental disorders characterized as a sodium channel protein type 1 subunit alpha (Scn1A)-related disorder. For example, SCn1A-related disorders include generalized epilepsy with fibrile seizures plus, intractable childhood epilepsy with generalized tonic-clonic seizures, intractable infantile partial seizures, myoclonic-astatic epilepsy, severe myoclonic epilepsy in infancy, simple febrile seizures, Lennox-Gastaut syndrome (LGS), infantile spasms, and vaccine-related encephalopathy and seizures by administering to a patient in need thereof a pharmaceutical composition of pipradrol or a pharmaceutically acceptable salt thereof.

The methods described herein may be particularly effective in subjects experiencing intractable seizures, status epilepticus, akinetic seizures, myoclonic seizures, absence seizures, or severe myoclonic epilepsy in infancy (SMEI).

Generally, the pipradrol or derivative thereof is administered to a patient diagnosed with a developmental disorder in a daily dosage range of about 0.1 mg to about 50 mg. In embodiments, an infant may be administered pipradrol or pharmaceutically acceptable salt thereof in a daily dosage range of about 0.2 mg to about 1 mg. In embodiments, a non-infant child may be administered pipradrol or pharmaceutically acceptable salt thereof in a daily dosage range of about 1 mg to about 5 mg. In embodiments, an adult may be administered pipradrol or pharmaceutically acceptable salt thereof in a daily dosage range of about 5 mg to about 10 mg.

DETAILED DESCRIPTION

Provided herein are methods and compositions for treating developmental disorders by administering to a patient in need thereof a pharmaceutical composition comprising pipradrol, a derivative thereof, or a pharmaceutically acceptable salt thereof. In embodiments, the methods and compositions described herein include pipradrol or a pharmaceutically acceptable salt thereof.

In embodiments, the methods described herein may be used to treat developmental disorders including epilepsy, Landau-Kleffner Syndrome, Lennox-Gastaut syndrome (LGS) and Dravet syndrome. In embodiments, the methods include treatment of Dravet syndrome.

In embodiments, the methods described herein may be used to treat developmental disorders including benign rolandic epilepsy (BRE), intractable childhood epilepsy (ICE), childhood absence epilepsy (CAE), juvenile myoclonic epilepsy (JME), infantile spasms (or West syndrome), generalized epilepsy with febrile seizure plus (GEFS+) and Lennox-Gastaut syndrome (LGS).

In embodiments, the methods described herein may be used to treat developmental disorders characterized as a sodium channel protein type 1 subunit alpha (Scn1A)-related disorder. For example SCn1A-related disorders include generalized epilepsy with fibrile seizures plus, intractable childhood epilepsy with generalized tonic-clonic seizures, intractable infantile partial seizures, myoclonic-astatic epilepsy, severe myoclonic epilepsy in infancy, simple febrile seizures, Lennox-Gastaut syndrome (LGS), infantile spasms, and vaccine-related encephalopathy and seizures.

The methods described herein may be particularly effective in subjects experiencing intractable seizures, status epilepticus, akinetic seizures, myoclonic seizures, absence seizures, or severe myoclonic epilepsy in infancy (SMEI). In embodiments, the disorders are characterized by intractable seizures. Intractable seizures (also referred to as "uncontrolled" or "refractory" seizures) are seizures that cannot be controlled with conventional treatments. For example, the subject can have intractable epilepsy or another disorder characterized by intractable seizures, or a disorder characterized by status epilepticus. Status epilepticus is a condition in which seizures follow one another without recovery of consciousness between them. Accordingly, in embodiments, the disclosed methods are used to treat subjects that are resistant to one or more conventional therapies.

The methods described herein may be particularly useful for treating children and infants, and for treating disorders that onset during infancy or childhood. In embodiments, the subject of the disclosed method is a newborn, a baby, a toddler, a preschooler, a school-age child, a tween, or a teenager. In embodiments, the subject is 18 years old or younger, 12 years old or younger, 10 years old or younger, 8 years old or younger, 6 years old or younger, 4 years old or younger, 2 years old or younger, 1 year old or younger. In embodiments, the subject is an adult that is over eighteen years old.

In embodiments, the developmental disorders are characterized by seizures associated with epilepsy. In embodiments, the seizures are non-epileptic seizures (NES) or dissociative seizures that are distinguished from epilepsy. Non-epileptic seizures include organic non-epileptic seizures and psychogenic seizures.

Epilepsy is a neurological disorder that occurs when nerve cell activity in the brain becomes disrupted, leading to seizures or periods of unusual behavior, sensations and sometimes loss of consciousness. A subject can be said to have epilepsy when having two seizures without an obvious cause. Epilepsy can occur in both adults and children, and can be associated with a specific syndrome. Accordingly, in embodiments, the subject has a childhood epilepsy syndrome such as benign rolandic epilepsy (BRE), childhood absence epilepsy (CAE), juvenile myoclonic epilepsy (JME), infantile spasms (or West syndrome), or Lennox-Gastaut syndrome (LGS).

In embodiments, the subject does not experience diagnosable seizures, but exhibits subclinical electrical discharges, which refers to a high rate of seizure-like activity when their brain waves are measured with an electroencephalogram. Epileptic syndromes associated with these seizure-like discharges include Landau-Kleffner Syndrome and Continuous Spike-wave Activity during Slow-wave Sleep.

In embodiments, the developmental disorders treated by the methods and compositions described herein include Scn1A-related seizure disorders. Scn1A-related seizure disorders include simple febrile seizures (FS) and generalized epilepsy with febrile seizures plus (GEFS+) at the mild end to Dravet syndrome and intractable childhood epilepsy with generalized tonic-clonic seizures (ICE-GTC) at the severe end. Specific Scn1A-related seizure disorders include, but are not limited to, generalized epilepsy with fibrile seizures plus, intractable childhood epilepsy with generalized tonic-clonic seizures, intractable infantile partial seizures, myoclonic-astatic epilepsy, severe myoclonic epilepsy in infancy, simple febrile seizures, Lennox-Gastaut syndrome (LGS), infantile spasms, and vaccine-related encephalopathy.

In embodiments, the subject has an intellectual developmental disability (IDD) such as an Autism Spectrum Disorders (ASD). In embodiments, the subject of the disclosed method has epilepsy and an IDD or ASD disorder. Common IDD and ASD that are comorbid with seizures and epilepsy include, but are not limited to, fragile X syndrome (FXS), Rett syndrome (RTT), Angelman syndrome, Prader-Willi syndrome, Velocardiofacial syndrome, Smith-Lemli-Opitz syndrome, neuroligin mutations and "interneuronopathies" resulting from aristaless-related homeobox, X-linked (ARX) and Nueropilin 2 (NRP2) gene mutations.

In embodiments, methods and compositions are provided for treating developmental disorders by administering to a patient in need thereof a pharmaceutical composition comprising pipradrol or a pharmaceutically acceptable salt thereof. In embodiments, compounds structurally related to pipradrol or a derivative or analog thereof are administered. Such compounds, can include, for example, desoxypipradrol, diphenylprolinol, 2-(diphenylmethyl)pyrrolidine, or pharmaceutically acceptable salts thereof.

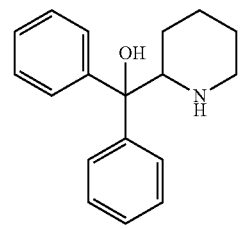

Pipradrol

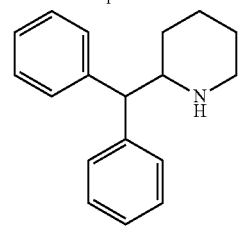

Desoxypipradrol

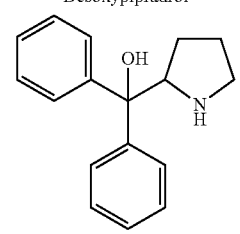

Diphenylprolinol

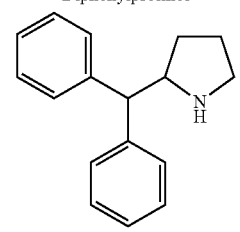

2-(Diphenylmethyl)pyrrolidine

Pipradrol, derivatives, analogues and structurally related compounds thereof useful in the disclosed methods includes any form of the compounds, such as the base (zwitter ion), pharmaceutically acceptable salts, e.g., pharmaceutically acceptable acid addition salts, hydrates or solvates of the base or salt, as well as anhydrates, and also amorphous, or crystalline forms.

In embodiments, deuterated pipradrol or deuterated forms of pipradrol derivatives may be used. Deuteration of pharmaceuticals to improve pharmacokinetics (PK), pharmacodynamics (PD), and toxicity profiles, has been demonstrated previously with some classes of drugs. Accordingly the use of deuterium-enriched pipradrol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched pipradrol.

Deuterium enriched pipradrol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments, deuterium enriched pipradrol means that the specified position is enriched with deuterium above the naturally occurring distribution (i.e., above about 0156%). In embodiments, deuterium enrichment is, e.g., no less than about 1%, no less than about 5%, no less than about 10%, no less than about 20%, no less than about 50%, no less than about 70%, no less than about 80%, no less than about 90%, or no less than about 98% of deuterium at a specified position. In embodiments, deuterium enrichment may be defined as, e.g., more than about 60%, more than about 65%, more than about 75%, more than about 80%, more than about 85%, more than about 95% deuterium at a specified position.

In embodiments, the pipradrol or a pharmaceutically acceptable salt thereof may include the racemic mixture, as well as compositions including each enantiomer individually. The compositions and methods contemplated herein may provide reduced dosing frequency, reduced adverse events and/or increased efficacy compared to a racemic mixture of pipradrol. In embodiments, compositions and methods that include each enantiomer individually may provide reduced dosing frequency, reduced adverse events and/or increased efficacy compared to the minor enantiomer. Thus, for example, contemplated herein are compositions and methods of treatment that provide the S enantiomer of pipradrol or a pharmaceutically acceptable salt thereof that is substantially free of the R enantiomer. In embodiments, methods and compositions herein include the R enantiomer of pipradrol or a pharmaceutically acceptable salt thereof substantially free of the S enantiomer. By "substantially free" it is meant that the composition includes less than 50% of the minor enantiomer. In embodiments, the compositions and methods herein may include less than about, e.g., 25%, 15%, 10%, 8%, 5%, 3%, 2%, or less than 1% of the minor enantiomer.

In embodiments, the methods and compositions include (S)-pipradrol, or a pharmaceutically acceptable salt thereof. In embodiments, the compositions include more than, e.g., about 75%, about 85%, about 90%, about 95% or about 98% (S)-pipradrol. In embodiments, the compositions include between, e.g., about 50% to about 75%, about 75% to about 100%, about 85% to about 100%, about 90% to about 100%, or about 95% to about 100% (S)-pipradrol.

In embodiments, the methods and compositions herein include (R)-pipradrol, or a pharmaceutically acceptable salt thereof. In embodiments, the compositions include more than, e.g., about 75%, about 85%, about 90%, about 95% or about 98% (R)-pipradrol. In embodiments, the compositions include between, e.g., about 50% to about 75%, about 75% to about 100%, about 85% to about 100%, about 90% to about 100%, or about 95% to about 100% (R)-pipradrol.

In embodiments, pipradrol or a pharmaceutically acceptable salt thereof is administered at dosages ranging from about 0.001 mg/kg and about 10 mg/kg of body weight of a patient in need thereof, e.g., from about 0.01 mg/kg to 2.0 mg/kg at least once a day. For example, dosages may include amounts of pipradrol or a pharmaceutically acceptable salt thereof in the range of about, e.g., 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.5 mg, 1.0 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 10 mg, 11 mg, 12 mg, 15 mg, 20 mg, 25 mg, and 30 mg being specific examples of doses.

Typically, dosages of pipradrol or pharmaceutically acceptable salts thereof are administered once or twice daily to a patient in need thereof. The methods and compositions described herein may provide reduced dosing frequency and reduced adverse events and/or increased efficacy. In embodiments, the dosage is about, e.g., 0.1-20 mg/day, or 0.2-15 mg/day, or 0.5-10 mg/day, or 0.75-5 mg/day, for example 0.2 mg/day, 0.5 mg/day, 0.75 mg/day, 1 mg/day, 1.5 mg/day, 2 mg/day, 3 mg/day, 4 mg/day, 5 mg/day, 6 mg/day, 7 mg/day, 8 mg/day, 9 mg/day, or 10 mg/day. In embodiments, pipradrol, or a derivative or analogue thereof is administered at doses of 0.2 mg to 1 mg in infants or 1-20 mg in adults, once daily.

Methods of treating developmental disorders by administering to a subject in need thereof an effective amount of pipradrol or a pharmaceutically acceptable salt, derivative or analogue, or combination thereof, are provided. An effective amount or therapeutically effective amount can be a dosage sufficient to treat, inhibit, or alleviate one or more symptoms of a developmental disorder such as reducing the frequency or severity of seizures, reducing behavior abnormalities (or otherwise improving behavior); or to provide a desired pharmacologic and/or physiologic effect, for example, reducing, inhibiting, or reversing one or more of the underlying pathophysiological mechanisms underlying the neurological dysfunction, increasing dopamine levels or signaling, or a combination thereof. The precise dosage will vary according to a variety of factors such as subject-dependent variables (e.g., age, immune system health, clinical symptoms etc.).

In embodiments, the methods described herein are effective to reduce, delay, or prevent one or more other clinical symptoms of a developmental disorder, particularly epilepsy or Dravet syndrome. For example, the effect of a composition including pipradrol or a pharmaceutically acceptable salt, derivative or analogue thereof on a particular symptom, pharmacologic, or physiologic indicator can be compared to an untreated subject, or the condition of the subject prior to treatment. In embodiments, the symptom, pharmacologic, and/or physiologic indicator is measured in a subject prior to treatment, and again one or more times after treatment is initiated. In embodiments, the control is a reference level, or average determined based on measuring the symptom, pharmacologic, or physiologic indicator in one or more subjects that do not have the disease or condition to be treated (e.g., healthy subjects). In embodiments, the effect of the treatment is compared to a conventional treatment that is known the art.

Pipradrol or a pharmaceutically acceptable salt, derivative or analogue thereof as described herein may be considered stimulants because they "stimulate" motor behavior. These effects may come at a cost, since, in certain instances, stimulants can increase agitation and anxiety, reduce sleep, and inhibit appetite. Moreover, many can be addictive and have abuse potential. At higher doses stimulants may induce convulsions. On the simplest level, a stimulant may be considered to be the opposite of a depressant, and depressants, such as barbiturates and benzodiazepines which may have robust anti-epileptic activity. Therefore, it is commonly believed that certain stimulants can be pro-convulsant and may typically be considered as contraindicated in the treatment of developmental disorders. Indeed, there is some clinical evidence that certain stimulants may lower the convulsive threshold in patients with prior history of seizures, in patients with prior electroencephalogram (EEG) abnormalities in the absence of seizures, and, rarely, in patients without a history of seizures and no prior EEG evidence of seizures. Accordingly, the methods and compositions described herein may surprisingly provide reduction in the frequency of seizures, the severity of seizures, or a combination thereof in a patient diagnosed with a developmental disorder.

In embodiments, compositions and methods of treatment are provided with low dosages of pipradrol such that the patient is provided one or more beneficial effects related to a developmental disorder, such as, reduced seizure activity, reduced fatigue, increased mood, increased concentration, increased behavioral control and/or increased cognitive ability. Pipradrol is known to have a relatively long half-life that may lead to prolonged effects and drug accumulation in a patient. Provided herein are dosing regimens that allow effective treatment of a developmental disorder with potentially limited or substantially few negative side effects, e.g., convulsions and/or sleep disruption. Accordingly, the methods described herein may provide treatment of a development disorder that may be considered surprising and unexpected. For example, methods are provided herein of treating developmental disorders in a patient in need thereof which may not cause sleep disruption. In embodiments, methods described herein may provide effective treatment of a development disorder without interrupting Slow Wave Sleep. In embodiments methods of treating a developmental disorder without causing insomnia or trouble falling asleep are provided.

The methods provided may also surprisingly and unexpectedly reduce or prevent seizures, or symptoms thereof in a subject in need thereof. The methods provided may reduce or prevent one or more different types of seizures. Generally, a seizure can include convulsions, repetitive movements, unusual sensations, and combinations thereof. Seizures can be categorized as focal seizures (also referred to as partial seizures) and generalized seizures. Focal seizures affect only one side of the brain, while generalized seizures affect both sides of the brain. Specific types of focal seizures include simple focal seizures, complex focal seizures, and secondarily generalized seizures. Simple focal seizures can be restricted or focused on a particular lobe (e.g., temporal lobe, frontal lobe, parietal lobe, or occipital lobe). Complex focal seizures generally affect a larger part of one hemisphere than simple focal seizures, but commonly originate in the temporal lobe or the frontal lobe. When a focal seizure spreads from one side (hemisphere) to both sides of the brain, the seizure is referred to as a secondarily generalized seizure. Specific types of generalized seizures include absences (also referred to as petit mal seizures), tonic seizures, atonic seizures, myoclonic seizures, tonic clonic seizures (also referred to as grand mal seizures), and clonic seizures.

In embodiments, methods described herein may reduce the frequency of seizures, reduce the severity of seizures, change the type of seizures (e.g., from a more severe type to a less severe type), or a combination thereof in a subject after treatment compared to the absence of treatment (e.g., before treatment), or compared to treatment with an alternative conventional treatment.

It is believed that the disclosed compounds, such as pipradrol, pharmaceutically acceptable salts, derivatives and/or analogues thereof, can be used as a monotherapy as the only active agent. In embodiments, methods are provided of treating development disorders using pipradrol or a pharmaceutically acceptable salt thereof in a pharmaceutically acceptable carrier. In embodiments, methods of treating development disorders include administration of pipradrol, pharmaceutically acceptable salts, derivatives and/or analogues thereof in combination with one or more other active compounds. The combination therapies can include administration of the active agents together in the same admixture, or in separate admixtures. In embodiments, the pharmaceutical composition includes two, three, or more active agents. In embodiments, the combinations result in a more than additive effect on the treatment of the disease or disorder. Thus, treatment is provided of a developmental disorder with a combination of agents that combined, may provide a synergistic effect that enhances efficacy.

In embodiments, the compound is administered in combination with conventional therapy for seizures, epilepsy, or one of the other disorders disclosed herein. For example, common conventional therapies for seizures and epilepsy include antiepileptic drugs and non-antiepileptic drug treatments such as low carbohydrate diet (e.g., ketogenic diets, such as classical diet, medium chain triglyceride (MCT) diet, modified Atkins diet (MAD), and low glycemic index treatment (LGIT)), intravenous immunoglobulin, steroids, elimination diet, valgus nerve stimulation, corticetomy, and multiple subpial transections.

Common antiepileptic and anticonvulsive active compounds that may be used in combination with pipradrol include, but are not limited to, acetazolamide, carbamazepine, clobazam, clonazepam, eslicarbazepine acetate, ethosuximide, gabapentin, lacosamide, lamotrigine, levetiracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

In embodiments, the disclosed methods include administering to a subject pipradrol in combination with gaboxadol. Gaboxadol, derivatives, analogues and structurally related compounds thereof useful in the disclosed methods includes any form of the compounds, such as the base (zwitterion), pharmaceutically acceptable salts, e.g., pharmaceutically acceptable acid addition salts, hydrates or solvates of the base or salt, as well as anhydrates, and also amorphous, or crystalline forms. In embodiments, a co-therapy of pipradrol or a derivative thereof and gaboxadol or a derivative thereof is effective to reduce seizure frequency or severity in the subject greater than either compound is administered alone. In embodiments, the co-therapy produces a more than additive result compared to compounds administered individually.

In general, by way of example, dosage forms useful in the disclosed methods can include doses of gaboxadol, derivatives, analogues and structurally related compounds thereof in the range of 0.1 to 20 mg, 1 to 15 mg, 5 to 20 mg, 7.5 to 25 mg, or 10 to 30 mg, or 12.5 to 20 mg, or 15 to 25 mg, or 10 to 40 mg, or 5 to 50 mg, or 22.5 to 60 mg, or 25 to 50 mg, with doses of 1 mg, 5 mg, 10 mg, 15 mg, 20 mg, 25 mg, 30 mg, 35 mg, 40 mg, 45 mg, 50 mg, 55 mg, 60 mg, 75 mg, and 100 mg. Typically, such dosages are administered once, twice, or three times daily, or every other day to, e.g., a human.

An exemplary oral dose form may include from about 2.5 mg to about 30 mg gaboxadol. In embodiments, gaboxadol is in a crystalline form. In embodiments of the medicament may include an effective amount of gaboxadol from 2.5 mg to 20 mg, such as 2.5 mg to 4 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg, e.g. 2.5 mg, 5 mg, 7.5 mg, 10 mg, 12.5 mg, 15 mg, 17.5 mg, or 20 mg. An exemplary embodiment may include about 5 mg to about 20 mg of crystalline gaboxadol, such as the hydrochloride of gaboxadol. In embodiments, the total amount administered to a subject in 24-hour period is 1 mg to 50 mg. In embodiments, the subject may be started at a low dose and the dosage is escalated. In this manner, it can be determined if the drug is well tolerated in the subject. Dosages can be lower for children than for adults.

In embodiments, such as combination therapies, a dose of gaboxadol for children can be 0.1 mg/kg to 1 mg/kg, and the dose for pipradrol may be 0.01 mg/kg to 0.1 mg/kg. The weight/weight ratio of gaboxadol and pipradrol is can be 10-to-1. However, the dosing ratio based on milligrams of active pharmaceutical ingredient (API) can range from 0.1-to-1 to 100-to-1 of gaboxadol-to-pipradrol respectively.

Effective treatment of a developmental disorder (e.g., SMEI or Dravet syndrome) herein may be established by showing reduction in the frequency of seizures (e.g., more than 50%) after a period of time compared with baseline. For example, after a baseline period of 1 month, the patients may be randomly allocated pipradrol or placebo as add-on therapy to standard therapies, such as valproate and clobazam, during a double-blind period of 2 months. Primary outcome measurements may include the percentage of responders on pipradrol and on placebo, defined as having experienced at least a 50% reduction of clonic (or tonic-clonic) seizure frequency during the second month of the double-blind period compared with baseline. Patients who present with status epilepticus during the double-blind period may be regarded as non-responders. Secondary outcomes may include the absolute count of clonic (or tonic-clonic) seizures during the second month of the double-blind period (normalized to 30 days, by dividing the raw count by the exact number of days of observation and multiplying by 30) and the percentage of change from baseline.

The effectiveness of pipradrol for the treatment of a disclosed developmental disorder, e.g., associated with Lennox-Gastaut syndrome, may be established in other controlled studies. For example, a randomized, double-blind, placebo-controlled study consisting of a 4-week baseline period followed by a 3-week titration period and 12-week maintenance period may be used in patients age 2-54 years with a current or prior diagnosis of LGS. Multiple target maintenance doses of pipradrol may be tested according to patient body weight and specific dosing regime. A primary efficacy measure may include the percent reduction in the weekly frequency of drop seizures (atonic, tonic, or myoclonic), also known as drop attacks, from the 4-week baseline period to 12-week maintenance period. Thus, efficacy may be measured as percentage reduction in weekly seizure (e.g., atonic, tonic, or myoclonic) frequency from baseline of, e.g., 0 to <20, 20 to <40, 40 to <60, 60 to <80, 80 to <100.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In embodiments, treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" may also refer to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As used herein, the term "prevention" or "preventing" means to administer a composition to a subject or a system at risk for or having a predisposition for one or more symptoms caused by a disease or disorder to facilitate cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" are used herein interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

"Stereoisomer", as used herein, refers to isomeric molecules that have the same molecular formula and sequence of bonded atoms (constitution), but which differ in the three dimensional orientations of their atoms in space. Examples of stereoisomers include enantiomers and diastereomers. As used herein, an enantiomer refers to one of the two mirror-image forms of an optically active or chiral molecule. Diastereomers (or diastereoisomers) are stereoisomers that are not enantiomers (non-superimposable mirror images of each other). Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2 n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Enantiomers and/or diasteromers can be resolved or separated using techniques known in the art. "Chirality" also includes axial and planar chirality.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods.

Those skilled in the art will recognize, or be able to ascertain using no more than routine experimentation, many equivalents to the embodiments described herein. Such equivalents are intended to be encompassed by the following claims.

What is claimed is:

1. A method of treating Dravet syndrome comprising administering to a patient in need thereof a pharmaceutical composition comprising about 0.1 mg to about 50 mg pipradrol or a pharmaceutically acceptable salt thereof.

2. The method of claim 1 wherein the composition provides reduction in the frequency of seizures, the severity of seizures, or a combination thereof in a patient diagnosed with Dravet syndrome.

3. The method of claim 1 wherein the compound is administered to the patient a daily dosage in the range of about 0.1 mg to about 50 mg pipradrol or a pharmaceutically acceptable salt thereof.

4. The method of claim 1 further comprising administering a second compound selected from the group consisting of gaboxadol, acetazolamide, carbamazepine, clobazam, clonazepam, eslicarbazepine acetate, ethosuximide, gabapentin, lacosamide, lamotrigine, leviteracetam, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

* * * * *